United States Patent [19]

Steppe

[11] Plant 3,993

[45] Dec. 21, 1976

[54] PINK SACHET-PINK FLOWERING DOGWOOD TREE

[76] Inventor: Clarence M. Steppe, 3800 New Bern Ave., Raleigh, N.C. 27610

[21] Appl. No.: 615,502

[22] Filed: Sept. 22, 1975

[51] Int. Cl.[2] ..... A01H 5/00

[52] U.S. Cl. ..... Plt./51

[58] Field of Search ..... Plt./51

*Primary Examiner*—Robert E. Bagwill

*Attorney, Agent, or Firm*—Burns, Doane, Swecker & Mathis

[57] ABSTRACT

The invention relates to a new and distinct variety of pink flowering dogwood tree, botanically known as *Cornus florida rubra*, which most nearly resembles the Cherokee Chief variety. In constrast to this known variety the new variety exudes from its flowers a strong fragrance generally resembling the composite fragrance of gardenia, honeysuckle and calycanthus.

1 Drawing Figure

DESCRIPTION OF NEW VARIETY

The present new and distinct variety of pink dogwood tree was discovered by me growing in a cultivated area. More specifically, the tree was found growing in a nursery bed on property of Wayside Nurseries at Raleigh, N.C. among a group of trees of the Cherokee Chief variety (U.S. Plant Pat. No. 1,710) of *Cornus florida rubra*. The exact origin of the plant is unknown. Since the plant was located in a bed which had been treated with radio-active phosphorus approximately ten years earlier, it is believed that the modification (described hereafter) may have come about as a genetic change due to radio-activity.

As the subject dogwood tree grew over the years my attention was directed to it primarily because of its pronounced flower fragrance which readily may be detected when flowers are present by those passing adjacent thereto even when passersby have not been alerted to the presence of the improved variety. Of all of the plants in the bed only this one exhibited the pronounced fragrance.

Because of the distinctive characteristics of the new variety the plant was asexually reproduced by grafting at Raleigh, N.C. Continued observations and tests of the original plant and of the progeny thereof over a period of years have demonstrated that the unique flower fragrance and other characteristics (described hereafter) come true and are established and transmitted through succeeding propagations. All of the specimens described herein were grown and observed at Raleigh, N. C.

FIGS. I and II illustrate the blossoms of a representative young tree of the new and distinct variety.

Except where noted the new and distinct variety has characteristics substantially similar to the Cherokee Chief variety. Where there is reference to color, the ordinary dictionary meaning of terms is intended.

Growth habits: Vigorous and reasonably compact. It has also been noted that the new and distinct variety appears to be more drought resistant than Cherokee Chief plants growing in the same area.

Blooming habits: This cultivar blooms a few days later than the Cherokee Chief variety and has a richer rose coloring as it initially blooms fading to the approximate color of the Cherokee Chief variety. The flowers are extremely large and are approximately 3 to 4.5 inches in diameter. The flower has two large rounded petals and two slightly ovate petals which are fuller and broader and less ovate than the Cherokee Chief variety.

Branching habits: Resembles the Cherokee Chief variety except that it tends to be more spreading.

Foliage: New foliage in the spring is suffused with a bronzy magenta rose very similar to the Cherokee Chief variety. The leaves are 4.5 to 5.5 inches in length and 2.5 to 3.5 inches in width and are somewhat larger than the Cherokee Chief variety.

Hardiness: Good. This tree has undergone temperatures of 10° below zero with no apparent damage.

Fragrance: This is the prime distinguishing characteristic of the new variety. Unlike the Cherokee Chief variety, this variety when flowering emits a pronounced fragrance which resembles a composite fragrance of gardenia, honeysuckle and calycanthus. All blossoms observed over a period of years have had this distinctive characteristic.

Having thus described and illustrated my new variety of dogwood tree what is claimed as new and desired to be secured by Letters Patent is:

1. A new and distinct variety of pink flowering dogwood tree, botanically known as *Cornus florida rubra*, substantially as illustrated and described, which most nearly resembles the Cherokee Chief variety, but being uniquely distinguished therefrom by the pronounced fragrance of its flowers generally resembling the composite fragrance of gardenia, honeysuckle and calycanthus.

* * * * *

PINK SACHET-PINK FLOWERING
DOGWOOD TREE
Filed Sept. 22, 1975
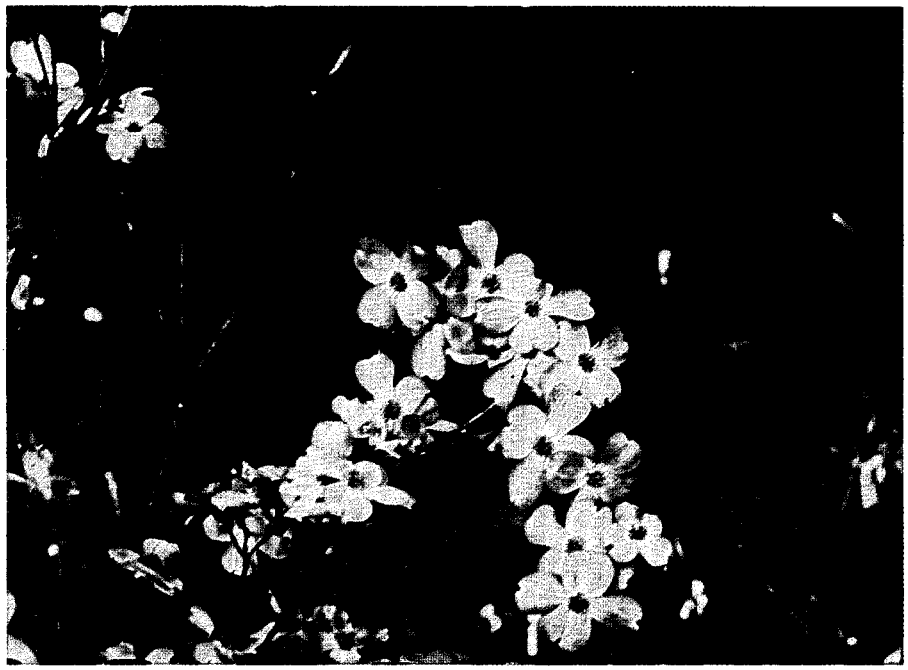
FIG. I
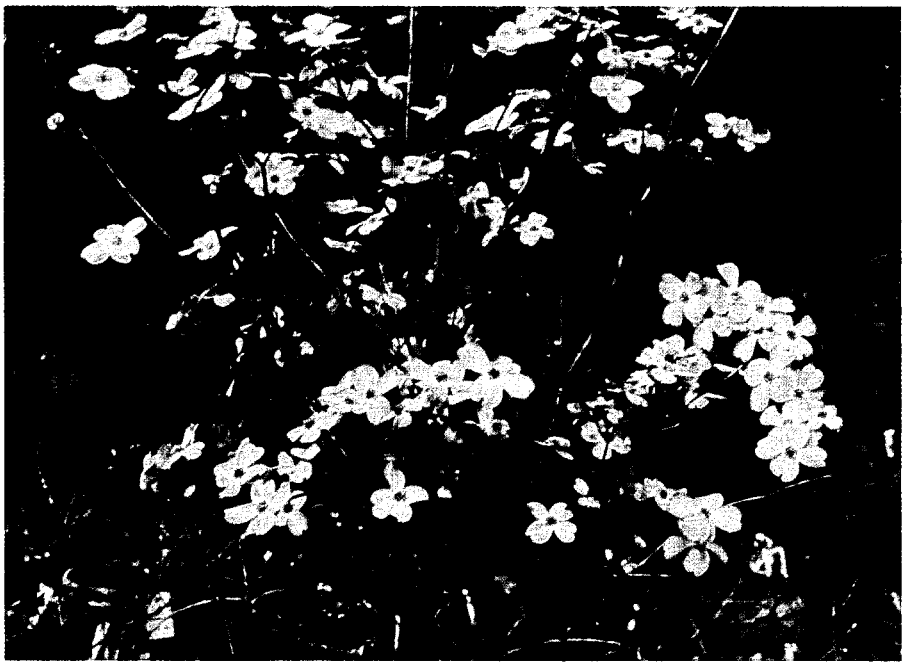
FIG. II